US00PP18306P3

(12) United States Plant Patent
Houbraken

(10) Patent No.: US PP18,306 P3
(45) Date of Patent: Dec. 11, 2007

(54) ***OSTEOSPERMUM* PLANT NAMED 'OSLIPU'**

(50) Latin Name: *Osteospermum ecklonis*
Varietal Denomination: Oslipu

(75) Inventor: Anna M. W. P. Houbraken, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/429,899

(22) Filed: May 8, 2006

(65) Prior Publication Data

US 2007/0261145 P1 Nov. 8, 2007

(51) Int. Cl.
*A01H 5/00* (2006.01)

(52) U.S. Cl. ..... Plt./360
(58) Field of Classification Search ..... Plt./360
See application file for complete search history.

(56) References Cited

U.S. PATENT DOCUMENTS

PP15,491 P3 * 1/2005 Oud ..... Plt./360

OTHER PUBLICATIONS

UPOV ROM GTITM Computer Database, GTI Jouve Retrieval Software 2006/04 Citation for 'Oslipu'.*

* cited by examiner

*Primary Examiner*—Wendy C. Haas
(74) *Attorney, Agent, or Firm*—Bruce Vrana

(57) ABSTRACT

A new and distinct cultivar of *Osteospermum ecklonis* plant named 'Oslipu' characterized by its very compact ball shape plant habit, dark green colored leaves, freely flowering with numerous inflorescences per plant, and daisy-type inflorescences with deep purple colored ray florets and blue colored disc florets.

1 Drawing Sheet

Latin name of the genus and species of the plant claimed: *Osteospermum ecklonis.*
Varietal denomination: 'Oslipu'.

BACKGROUND OF THE NEW PLANT

The present invention relates to a new and distinct cultivar of *Osteospermum* plant, botanically known as *Osteospermum ecklonis.*

The new *Osteospermum* is propagated by cuttings resulting from a cross of a proprietary *Osteospermum ecklonis* seedling selection as the male, or pollen, parent identified as code number 'C272' with a proprietary *Osteospermum ecklonis* selection identified as code number 'C298' as the female, or seed, parent. Breeding code of new plant is 'C0298-4.'

The new *Osteospermum* was discovered and selected as a single flowering plant within the progeny of the stated population grown in Enkhuizen, Netherlands, in 1998. Neither 'C272' nor 'C298' has been patented. The new *Osteospermum* plant has been repeatably asexually reproduced by cuttings in Enkhuizen, Netherlands over a period of 7 years. It has been found to retain its distinctive characteristics through successive propagations, and this novelty appears to be firmly fixed.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant. The data which defines these characteristics were collected from asexual reproductions carried out in Enkhuizen, Netherlands. The plant history was taken on 25 weeks old plants. The instant plant was grown indoors in a 10.5 cm container and transplanted into the open field in week 20.

Color references are primarily to the R.H.S. Colour Chart of The Royal Horticultural Society of London, edition 2001.

TABLE 1

DIFFERENCES BETWEEN THE NEW CULTIVAR 'OSLIPU' AND TWO SIMILAR CULTIVARS

| | 'Oslipu | 'Osoutis' (U.S. Pat. No. 15,491) | 'Wild Side' (Not patented) |
|---|---|---|---|
| Plant height | 18-20 cm | 25 cm | 38 cm |
| Plant width | 20-25 cm | 30 cm | 52 cm |
| Flower color | Purple fading | Purple fading | Deep Purple |
| Flower size | 4 cm | 5 cm | 5 cm |

The plant:

*Classification.*—Botanical: *Osteospermum ecklonis.*

Parentage:

*Female parent.*—A seedling named 'C298' is one of our seedlings from our C-generation of plants bred in 1998. Breeder's code of the new plant is 'C0298-4' (not patented).

*Male parent.*—A seedling named 'C272' is one of our seedlings from our C-generation of plants bred in 1998.

Plant description:

*Growth habit.*—Round, very compact.

*Plant height.*—18–20 cm.

*Speading area of plant.*—15–25 cm.
*Strength.*—Moderate growth.
*Branching character.*—Freely branching, 12 lateral branches without pinching.
*Blooming period.*—From May until October.

The stem:
*Length.*—13 cm.
*Diameter.*—2–3 mm.
*Internode length.*—10 mm.
*Texture.*—Glabrous.
*Color.*—RHS 146B.

The foliage:
*Shape.*—Single leaves, alternate and elliptic, apex: broadly acute. Base: attenuate, margin: irregular serration.
*Number of leaves per lateral branch.*—84.
*Texture.*—Glabrous, leather.
*Leaf.*—Color — Upper side: RHS 137B. Color — Under side: RHS 137C. Length: Young 10–16 mm, mature 50 mm. Width: Young 5–7 mm, mature 22–26 mm.
*Petiole.*—Absent.

The inflorescence:
*Number of inflorescences per mature plant.*—50.
*Inflorescence bud.*—Form: Ovoid. Length: 5–8 mm. Width: 6–8 mm. Color: RHS 79D.
*Inflorescence lastingness on the plant.*—Around 5 days depending on the temperature.
*Inflorescence.*—Diameter: 40 mm. Disc diameter: 6–8 mm.
*Inflorescence depth.*—6 mm.
*Fragrance.*—No fragrance.
*Disc florets.*—Shape: Tubular, elongated. Apex: Five pointed. Length: 8 mm. Width: 1 mm. Number of disc florets per inflorescence: 55. Color: RHS 79B.
*Ray florets.*—Length: 22 mm. Width: 6 mm. Shape: Capitulum with one series of ray florets. Color Upper surface: RHS 72A. Middle surface: RHS 72A. Lower surface: RHS N79A. Number of ray florets: 16–18, some (2–5) small needle ray florets per capitulum. Shape Apex: Rounded. Base: Acute. Margin: Entire. Texture: Satiny.
*Peduncles.*—Length: 4–5 cm. Texture: Tiny hairs. Color: RHS 144A. Diameter: 1.5 mm. Shape: Round.
*Phyllaries.*—Texture Rough, tiny hairs. Number of phyllaries: 16–17. Color: RHS 144B. Length: 7 mm. Margin: Entire. Width: 1 mm. Apex: Acute. Shape: Ligulate. Color: — Upper RHS 144B. Color: — Lower RHS 144B.

Reproductive organs:
*Androecium.*—Appearance: Present on disc florets only. Shape: Oblong, five stamens fused to one. Length: 2 mm. Width: 1 mm. Pollen color: RHS 25A. Total no. of anthers: 40.
*Gynoecium.*—Appearance Present on both ray and disc florets. Pistil number: One pistil per ray or disc floret. Pistil length: 4 mm. Stigma color: RHS 77A. Stigma shape: Bipartite.

Seed development: Seed development has been observed on plants of the new *Osteospermum.*
*Amount of seeds produced.*—Moderate.
*Seed length.*—5 mm.
*Diameter.*—2 mm.
*Color.*—RHS 200A.
*Shape.*—Elliptic.

Disease resistance: Under commercial conditions, plants of the new *Osteospermum* are resistant to fungal pathogens common to *Osteospermum.*

What is claimed is:

1. A new and distinct variety of *Osteospermum* plant, substantially as illustrated and described herein.

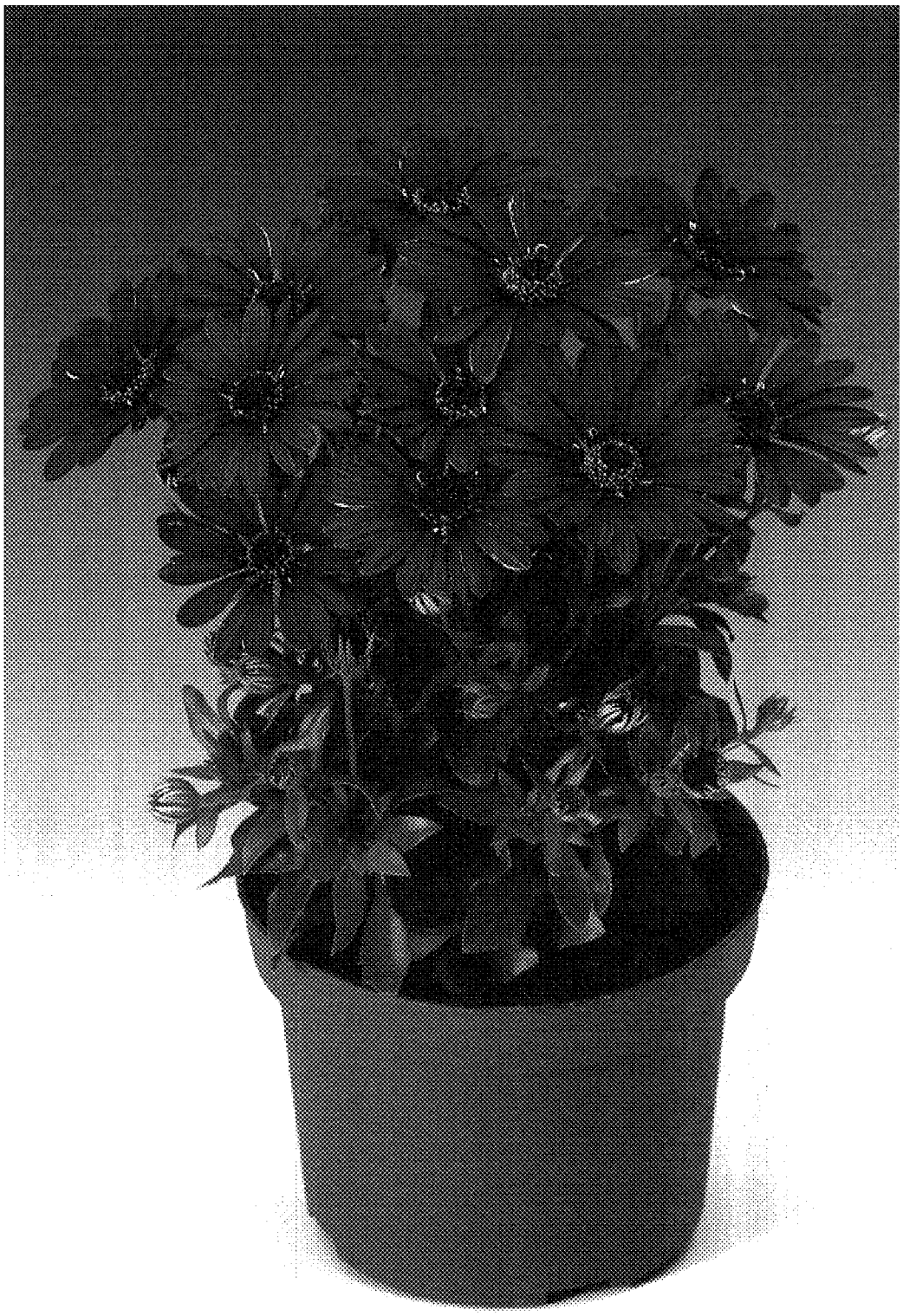

* * * * *